US006966904B2

(12) United States Patent
Ruth et al.

(10) Patent No.: US 6,966,904 B2
(45) Date of Patent: Nov. 22, 2005

(54) FEEDING DEVICE AND FEEDING METHOD FOR INFANTS

(76) Inventors: Anthony M. Ruth, 7213 Whispering Oak Dr., Sylvania, OH (US) 43560; Amy K Ruth, 7213 Whispering Oak Dr., Sylvania, OH (US) 43560

( * ) Notice: Subject to any disclaimer, the term of this patent is extended or adjusted under 35 U.S.C. 154(b) by 191 days.

(21) Appl. No.: 10/403,931

(22) Filed: Mar. 31, 2003

(65) Prior Publication Data

US 2004/0188372 A1 Sep. 30, 2004

(51) Int. Cl.[7] ............................................ A61M 31/00
(52) U.S. Cl. ..................................................... 604/514
(58) Field of Search ............................ 604/77, 73, 514, 604/74, 75, 76; 606/234–236

(56) References Cited

U.S. PATENT DOCUMENTS

| | | | |
|---|---|---|---|
| 3,790,016 | A | 2/1974 | Kron |
| 3,895,533 | A | 7/1975 | Steier |
| 4,232,687 | A | 11/1980 | Anderson-Shanklin |
| 4,834,099 | A | 5/1989 | Schrooten |
| 4,966,580 | A | 10/1990 | Turner et al. |
| 5,611,776 | A | 3/1997 | Simmons et al. |
| 5,830,235 | A | 11/1998 | Standley |
| 6,033,367 | A | 3/2000 | Goldfield |
| 6,120,528 | A | 9/2000 | Link et al. |
| 6,454,788 | B1 | 9/2002 | Ashton |

*Primary Examiner*—Manuel Mendez
(74) *Attorney, Agent, or Firm*—David C. Purdue; John C. Purdue

(57) ABSTRACT

A feeding device and a method for facilitating the transition from non-oral tube feeding to oral feeding is disclosed. The device comprises a fluid reservoir having a fluid outlet, a nipple having a fluid outlet, a shield attached to the nipple base, a conduit for conveying fluid from the reservoir to the nipple fluid outlet and a manually adjustable valve that is operable to prevent and control the flow of fluid through the conduit. The method comprises the steps of providing a device of the type just described, acclimating an infant to the device by closing the valve and inserting the nipple into the infant's mouth. The valve is then opened to permit the very slow flow of fluid through the nipple outlet. Additional feeding regimens are provided in which restriction of the flow of fluid is gradually relaxed over a series of feedings until the infant is able to withdraw about sixty cubic centimeters of fluid during a twenty minute feeding without distress.

2 Claims, 3 Drawing Sheets

FEEDING DEVICE AND FEEDING METHOD FOR INFANTS

BACKGROUND OF THE INVENTION

1. Field of the Invention

The present invention is generally directed to a feeding device for infants and a method for weaning infants, especially premature neonates as well as post surgical infants and medically fragile infant patients, from non-oral tube feeding to oral feeding from a bottle.

2. Description of the Prior Art

In many neonatal intensive care units, premature neonates first receive nutrition through a nasogastric or orogastric feeding tube, because these infants are incapable of coordinating the suck, swallow and breathe cycle required to receive oral nutrition. The transition from tube feeding to oral nutritive feeding is often quite traumatic. Infants are presented with a bottle and often the rate of liquid flow is too rapid for the infant to initiate a timely swallow in coordination with breathing. Consequently, these infants become distressed because they are overwhelmed by too much fluid being introduced at too high of a flow rate and may gag, choke or aspirate. These infants are returned to a non-oral tube feeding regimen until a physician decides that it is time to attempt bottle feeding again. In some cases this cycle continues to the detriment of these infants who may well develop aversions to oral feeding.

U.S. Pat. No. 3,790,016 (Kron) discloses an infant nursing device comprising a liquid chamber, a nipple, an air inlet passage for the chamber, a liquid metering passage between the chamber and an exterior portion of the nipple and may include a pressure transducer or a differential transducer. The device may include a valve for opening and closing the liquid metering passage in response to sensed conditions. The nipple may be solid except for the liquid metering passage or hollow so long as the flow of liquid out of the nipple is not responsive to compression of the nipple.

U.S. Pat. No. 6,033,367 (Goldfield) discloses a smart bottle and system for neonatal nursing development. According to the Goldfield patent, the system can be used to diagnose or monitor the sucking/swallowing/breathing competence of an impaired neonate or post-operative infant. The system includes a liquid feeding valve which controls the supply of nutrients through a feeding nipple via a processor. The processor operates to restrict or close the valve when slowing or cessation of breathing is detected or acts as a training device to set or pace, or initially to develop basic sucking/swallowing/breathing competence. The processor is also operable to control liquid flow to a level appropriate to the available sucking activity or to change the flow rate to maintain a stable and non-slowing breath rate. The processor is further operable to display an output that reflects the infant's breathing so that a care giver can manually operate a pressure bulb to rhythmically activate a pressure operated stimulator in the nipple.

SUMMARY OF THE INVENTION

The invention is based on the discovery of a feeding device and a method for facilitating the transition from non-oral tube feeding to oral feeding, particularly in premature neonates and medically fragile infants. The device comprises a fluid reservoir having a fluid outlet, a nipple having a fluid outlet, a shield attached to the nipple base to aid in forming a seal around an infant's mouth, a conduit for conveying fluid from the reservoir to the nipple fluid outlet and a manually adjustable valve associated with the conduit that is operable to prevent the flow of fluid through the conduit and to control the flow rate of fluid through the conduit. Preferably, the nipple is one that does not expel fluid when it is compressed but only expresses fluid when negative pressure is applied around the nipple outlet.

The method of the present invention comprises the steps of providing a device of the type just described, acclimating an infant to the device by closing the valve and inserting the nipple into the infant's mouth for a period of time to establish a functional and coordinated non-nutritive sucking pattern. The valve is then opened to permit the flow of fluid through the nipple outlet while restricting the flow of fluid so that, no matter how hard an infant sucks, the infant isn't able to withdraw fluid at a rate greater than a given rate, wherein the given rate is the rate that an infant with poor coordination of the sucking, swallowing and breathing cycle can handle without distress. The method comprises additional feeding regimens in which, if the infant didn't receive fluid at a rate that exceeded the infant's ability to swallow that fluid, restriction of the flow of fluid is gradually relaxed over a series of feedings until the infant is able to withdraw about sixty cubic centimeters of fluid during a twenty minute feeding without distress. If an infant suffers distress from receiving too much fluid at too fast of a rate, the flow is quickly restricted until the infant is able to coordinate the suck/swallow/breathe cycle and feed without distress.

It is an object of the invention to provide an elegantly simple device that will facilitate the transition between non-oral tube feeding and oral feeding for physically challenged infants, especially premature neonates and medically fragile infants.

It is a further object of the invention to provide a method for weaning an infant from non-oral tube feeding to oral nutritive feeding.

It is yet another object of the invention to provide a device that is extremely easy to use and that can be used without causing distress to an infant, especially an infant whose sucking ability exceeds the infant's ability to swallow.

It is a still further object of the invention to provide a device and a method that gives an infant time to burst and pause without expressing fluid at a flow rate that exceeds the flow rate that the infant can handle.

It is yet a further object of the invention to provide a method that does not assault the fragile sensory system of a premature neonate by delivering too much fluid at too high of a flow rate into the infant's mouth, which would increase the infant's risk of aspirating.

It is a further object of this invention to make it easy for multiple care givers, from skilled practitioners to parents with no previous experience with infant feeding, to participate in a consistent and efficacious method for weaning infants from non-oral tube feeding to oral nutritive feeding.

It is yet another object of this invention to foster the gradual development of coordinated sucking, swallowing and breathing cycles in infants as needed for successful oral nutritive feeding.

It is a still further object of this invention to provide a device for weaning infants from tube feeding that can be used successfully with infants who have the ability to suck in more fluid than they can swallow.

These and other objects and advantages of the present invention will become apparent to those skilled in the art upon a review of the following detailed description of the preferred embodiments and the accompanying drawings.

DETAILED DESCRIPTION OF THE PREFERRED EMBODIMENT

Figure 1:
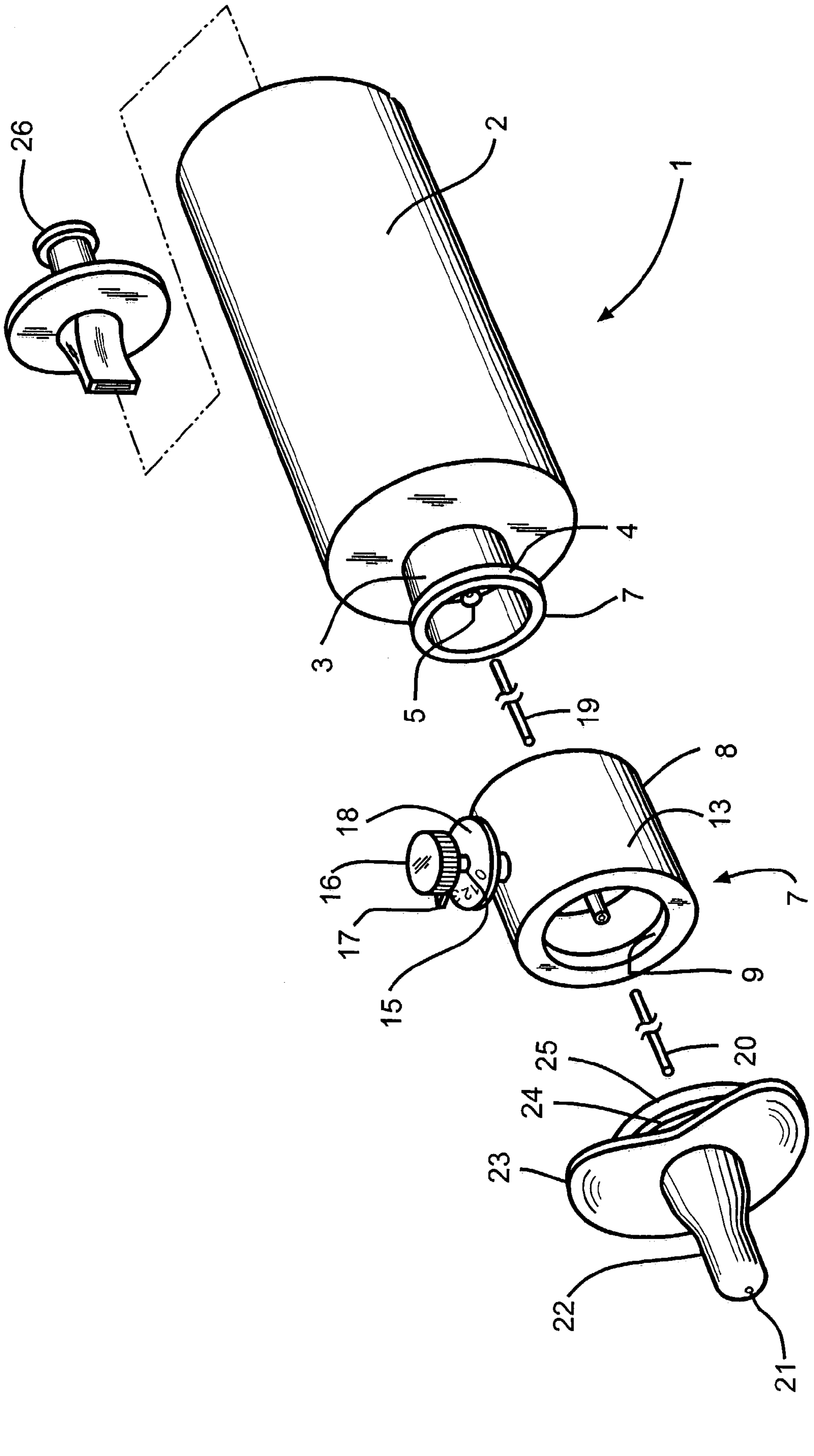
FIG. 1 is a perspective view of a feeding device according to the present invention.

The present invention is generally directed to a feeding device for infants and a method for weaning infants from non-oral tube feeding to oral feeding from a conventional bottle. More particularly, the feeding device and the method are used to gradually and safely promote the transition from non-nutritive sucking on a pacifier to nutritive sucking, i.e., a repetitive cycle of sucking, swallowing and breathing at a level or rate sufficient for an infant to intake at least about two ounces of nutritive fluid in a twenty minute session. The invention is particularly useful for premature infants that have not learned to coordinate the sucking, swallowing and breathing cycle sufficiently to enable them to take nutrition orally. The features of the invention will be more readily understood by referring to the attached drawing figures in combination with the following description.

When beginning to use the feeding device of the invention, the infant first establishes a functional non-nutritive suck with a pacifier. Oral feedings are then begun with the device delivering a minimum flow rate which is almost undetectable to an infant. The rate is gradually increased, preferably through an adjustable valve mechanism, or through a slide lock device such as ones that are used to control the flow rate of fluids that are being administered intravenously or through the use of different size tubing within the device. This progression allows an infant to gradually transition to faster flow rates without overwhelming the infant's delicate sensory system, thereby facilitating the gradual coordination of a functional suck/swallow/breathe pattern required for oral feeding from conventional bottles. If the infant is unable to achieve enough negative draw around the nipple to withdraw formula independently, the caregiver may assist by manually squeezing the bottle to express a small amount of liquid through the nipple. Alternatively, this can be achieved using an electric pump or a manual bulb type pump that can deliver a small amount of pressure with one measurable compression of the bulb connected to the end of the bottle which allows the caregiver to monitor exactly how fast and how much formula is being expressed. If desired, automated pump means may be provided to create a minimal positive pressure inside of a fluid reservoir of the device The act of nutritive sucking via bottle feeds is not typically initiated in premature infants until about 34 weeks after conception. Nutrition is provided to these neonates through a variety of invasive methods including intravenous, oral gastric and nasogastric tube feedings. These infants often develop a functional non-nutritive suck in an attempt to calm and organize their systems. The introduction of nutritive feeding, however, can be extremely traumatic and over stimulating to the neonate when liquids are presented at rate that is too rapid so as be overwhelming to the infant's sensory system. When liquids are introduced in a manner that is too fast or over stimulating, infants and neonates often cannot tolerate oral feeding and may develop aversion to oral feeding. In addition, these unsafe feeding experiences may place the infant further at risk for medical complications such as aspiration, respiratory compromise and failure to thrive. In addition, the caregiver frequently becomes stressed by these negative feeding experiences which may lead to a discontinuation of oral feeding altogether. This can further inhibit and delay the healthy development of the neonate at a time when it is absolutely critical that the transition to oral feeding is initiated.

The more negative experiences an infant has unsuccessful efforts at oral nutritive feeding, the greater the risk of feeding aversion becomes. In prior art methods, when a pacifier is removed, the established pattern of non-nutritive sucking is disrupted and this decreases the chances of establishing a functional nutritive sucking pattern on a nipple.

Many infants can develop a functional non-nutritive suck around a pacifier, but become extremely disorganized when the pacifier is removed and a bottle is introduced. The present device eliminates this disruption because it allows the infant to establish a functional non-nutritive suck around the pacifier nipple of the feeding apparatus and, without removing the pacifier, formula or breast milk is then introduced through the nipple at an extremely slow rate which is almost undetectable, to gradually prepare the sensory system as well as the respiratory system to coordinate a functional suck/swallow/breathe pattern. As the infant gains success, the flow rate is gradually increased at an almost undetectable rate so the infant does not become overwhelmed and stressed.

The pacifier has a straight nipple configuration to facilitate central grooving of the tongue. This reduces the potential for tongue thrusting motion during fluid expression, which can result in a poor seal around the nipple, causing fluid to leak from the infant's mouth.

The manual valve mechanism, a slide lock (as described previously) or the ability to control the flow rate by using different size tubes within the nipple is the key to the invention to introduce nutritive feeding in a slow, graduated and easily controlled manner. The precise, repeatability that can be achieved by using the valve or a flow rate control device allows for consistency of flow rates between caregivers. This is very important because neonates in a Neonatal Intensive Care Unit (NICU) or Pediatric ICU will have a multiple of different caregivers. This device will prove to be not only beneficial to the neonate's healthy transition to standard or conventional nipple flow rates, but also very helpful to the caregiver in the incredibly demanding atmosphere of a NICU or Pediatric ICU as well as an unskilled caregiver or parent when an infant is discharged to home. It also allows for a systematic, slow progression of flow rate with successful feedings. As the infant becomes successful with nutritive sucking at a slow flow rate over several feedings, the rate can be gradually increased so that it is nearly undetectable to the infant. This gradually trains the infant's oral motor, sensory and respiratory systems to adjust to a faster rate of flow in a highly controlled and consistent manner in preparation for nutritive feedings at a regular flow rate from a standard nipple. So much so that it can over time be medically prescribed based on historical results with similar patients and somewhat exacting "programs" can be adopted to greatly increase the success of oral feeding for infants and neonates. For example if a feeding regimen with a flow rate of "1" (or slowest possible rate) for about 20 minutes is prescribed for a few feedings, it can be administered consistently between caregivers and precisely increased to a "2" (or slightly faster flow rate) when the infant or neonate has mastered the flow rate of "1". While normal healthy babies rarely would need this type of feeding regimen, the incredibly delicate state of a premature baby, post surgical infant or medically fragile infant may require it.

Another key component of the invention is the use of a large reservoir which allows an infant to ingest up to two fluid ounces without interruption to refill the feeding apparatus. This is particularly important because an interruption affects not just the suck/swallow/breathe pattern but also the "burst and pause" portion of the infant feeding process. This is critical and it is highly documented that the pause portion allows the infant to calm and organize. It is critical that this cycle not be interrupted because it can be very detrimental to the infant's immediate and possibly long term ability to successfully thrive at the oral feeding process. In other words, if the nipple is removed from an infant's mouth to refill a reservoir, it is very detrimental to the process of developing the suck, swallow, breathe, burst and pause process required for successful oral nutritive feeding. While the process seems ridiculously easy to an average adult or child, it is a most daunting and difficult process for premature and medically fragile infants.

In one embodiment of the invention, fluid can be manually or automatically expressed by a caregiver from the reservoir to the nipple fluid outlet, in case the infant is unable to achieve enough negative pressure around the nipple to express formula independently. The optional pump features previously described enable the caregiver to consistently measure the rate at which fluid is being expressed to further help maintain consistency between caregivers.

Turning now to FIG. 1, a feeding device according to the invention is indicated generally at 1 and includes a reservoir 2 that can be a bottle type of container that is frequently used to feed infants. The reservoir 2 has a cylindrically shaped neck 3 extending from one end with a flange 4 extending outwardly from the neck 3. Inside of the neck 3 is a fluid outlet indicated at 5 for the reservoir 2 and the outlet 5 is defined by an axially extending flange 6. The reservoir 2 can be made of a compressible material such as plastic so that the reservoir 2 can be compressed to create a positive pressure in the reservoir 2. Alternatively, the reservoir 2 can be formed of a rigid material. Fluid may also be contained within a plastic bag carried within the reservoir 2, if desired.

Figure 2:
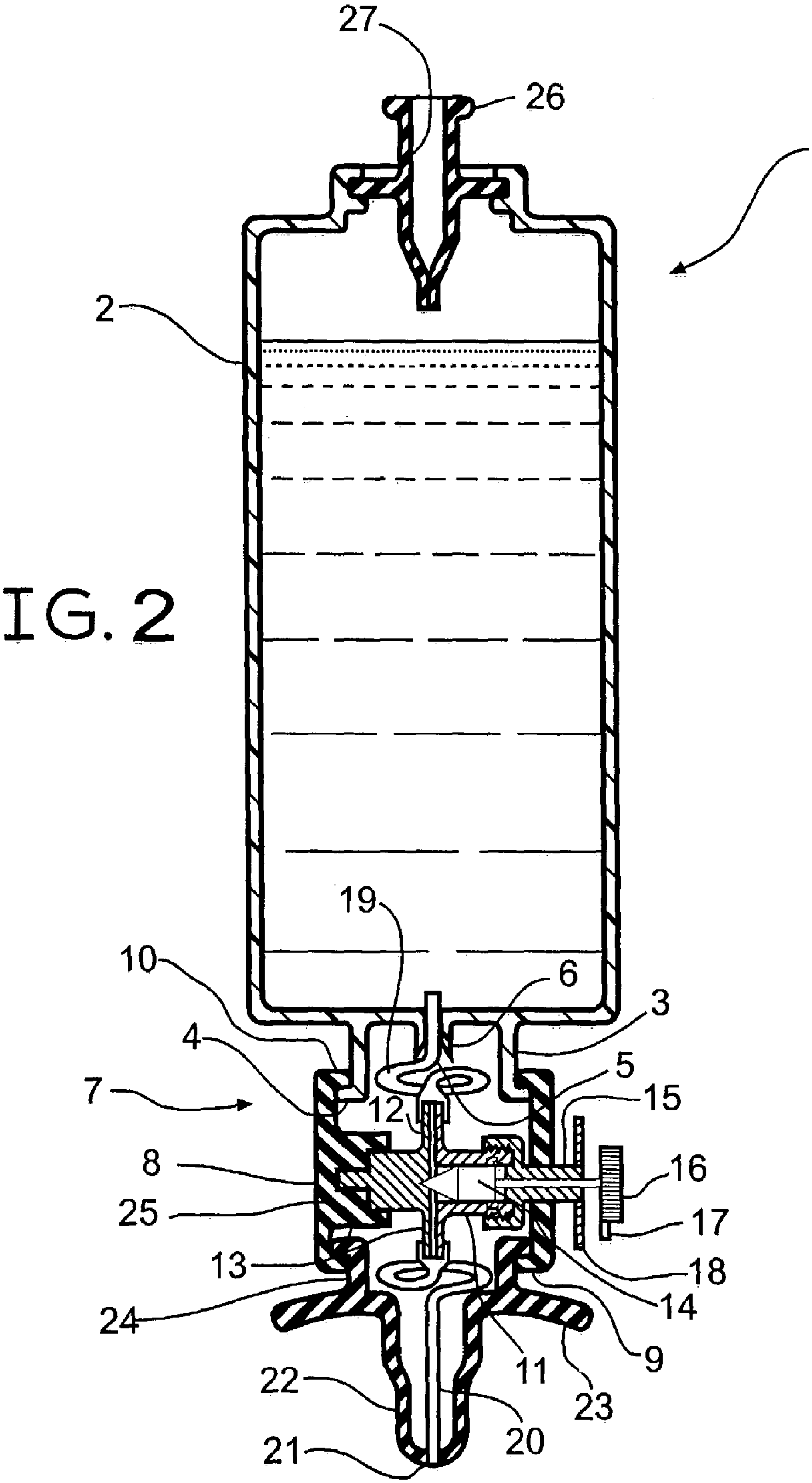
FIG. 2 is a view, mostly in cross-section, of the feeding device shown in FIG. 1.

A valve device indicated generally at 7 has a housing 8 that is generally cylindrical in shape with an inwardly extending flange 9 at one end and an inwardly extending flange 10 at the other end. The flange 10 of the valve housing 8 is operable to engage the flange 4 of the neck 3 of the reservoir 2, as shown in FIG. 2, to releasably connect the valve device 7 to the reservoir 2. The valve device 7 includes a valve body 11 having a fluid inlet 12 and a fluid outlet 13. A needle valve element 14 is axially movable within the valve body 11 and is operably connected to a valve stem 15 that is supported in the valve body 11 so that rotation of a valve stem 15 moves the needle 14 from a first position in which it closes communication between the fluid inlet 12 and the fluid outlet 13 and a second position in which there is communication between the inlet 12 and the outlet 13. In between the first and second positions, the needle 14 will restrict, more or less, the flow of fluid through the valve body 11. A knob 16 is supported on the valve stem 15 and includes a pointer 17. A valve face 18 with indicia representing various rotational positions of the valve stem 15 and corresponding axial positions of the needle 14, is supported below the knob 16 so that it cooperates with the pointer 17 to provide a user with an indication of whether the valve is open or closed and, if it is open, a quantitative or qualitative indication of the rate at which fluid will flow through the valve body 11 to the outlet 13. The valve body 11 may house a needle type valve, as shown, or another suitable flow rate controlling valve or other suitable device that can control the rate of flow of a fluid.

The fluid outlet 5 of the reservoir 2 is connected to the fluid inlet 12 of the valve body 11 by a small diameter tube 19. One end of the tube 19 has a frictional fit around the outside of the valve inlet 12 and the other end of the tube 19 has a friction fit within, the axially extending flange 6 on the reservoir. The small diameter tube 19 has an internal diameter from about 3 french to about 12 french, with a range from 5 french to about 8 french being preferred. It will certainly be appreciated that there are other ways to connect a valve or flow control device to the outlet of a reservoir. For example, the valve housing 8 can be formed integrally with the reservoir 2. The modular design of the device 1 is preferred, but other designs can be used to control the flow of fluid from the reservoir 2 to the valve inlet 12.

A small diameter tube 20 is connected to the fluid outlet 13 of the valve body 11 and carries fluid to a fluid outlet 21 in a nipple 22. A shield 23 is provided with the nipple 22 and the shield 23 is adapted to provide a seal around the lips of an infant so that when an infant has the nipple 22 in its mouth and its lips against the shield 23, the infant can suck and create a negative pressure operable to withdraw liquid into its mouth from the nipple outlet 21, through the tube 20 when the valve device 7 isn't closed. As shown in FIG. 2, a cylindrical flange 24 extends from the shield 23 and is provided with an outwardly extending flange 25. That flange 25 is operable to engage the flange 9 on the valve housing 8 to connect the nipple 22 and the shield 23 to the valve housing 8, in the same manner that the valve housing 8 is connected to the reservoir 2.

In some applications, it may be desirable to provide a plurality of feeding devices, similar to the feeding device 1, but without a valve device 7. Such a plurality of feeding devices would constitute a set and each include a reservoir for liquid and each would be provided with a different sized tube for conducting fluid from the reservoir to a nipple outlet. In such a set of feeding devices, the internal diameter of the connecting tube would effectively control the rate at which an infant can withdraw liquid from the device. Zero flow could be accomplished in one of the devices in a number of ways including not filling the reservoir and not including a tube at all. Alternatively, a single reservoir could be used with a plurality or set of nipples, each provided with a differently sized connecting tube. In either case, when it is desired to increase or decrease the flow rate of liquid to be supplied to an infant, the size of the connecting tube that is used in the feeding device can be changed. The flow rate for each size of connecting tube can be readily determined so that the appropriate tube is used for the particular feeding stage of the infant. In particular, once the infant is learning to feed, the size of the tube can be changed to adjust the rate at which liquid is supplied to the infant. Using a tube to control the flow rate in a set of feeding devices might reduce the cost of the feeding device and would make the part of the feeding device that comes into contact with the infant more practically a disposable product.

In a feeding device according to the invention, it is preferred to use a straight type of nipple such as the nipple 22. This most closely simulates a mother's nipple and facilitates an action known as central grooving of the tongue where an infant's tongue curves around the outside barrel of a straight nipple. As noted previously, the nipple 22 is preferably designed so that compression of the nipple doesn't cause fluid to be expelled from it. In the case of nipple 22, fluid is delivered to the outlet 21 through the tube 20 so that the nipple 22 doesn't fill up with liquid. If the nipple 22 did fill up with liquid, compression applied to the nipple would expel liquid within the nipple to be expressed. Accordingly, the tube 20 connecting the valve outlet 13 to the nipple outlet 21 makes the nipple 22 one that is configured so that compression of the nipple doesn't cause any significant quantity of fluid to be expelled from the nipple fluid outlet 21. This result can also be accomplished with a nipple (not shown) that is solid except for a small diameter liquid passageway connected to the nipple fluid outlet. In some cases, infants may be unable to tolerate even the very low flow rate of liquid through a straight nipple with a fluid outlet positioned at the end like the fluid outlet 21. In such cases, a nipple of the type disclosed in U.S. Pat. No. 6,454,788, the disclosure of which is incorporated herein by reference, may be employed. That nipple has a linear array of nipple fluid outlets arranged so as to direct fluid expelled from the nipple into physiologic gutters adjacent to the tongue, thereby possible avoiding stimulation of the gag reflex.

The reservoir 2 is provided with an air inlet valve 26, which is positioned in a fill passageway 27 provided on one end of the reservoir 2, opposite the end where the neck 3 is located. The air inlet valve 26 allows air to be drawn into the reservoir 2 so that a negative pressure doesn't develop inside the reservoir 2 when fluid is withdrawn therefrom. A negative pressure inside of the reservoir 2 can interfere with the delivery of fluid to the nipple outlet 21. A duckbill type of air valve 26 is especially well suited for use in the device 1. However, it will be clearly understood that other air valves, especially one way valves, can be utilized. When the air valve 26 is removed, the fill passageway 27 is open and can be used to fill the reservoir 2 with formula, breast milk or other beneficial fluids for an infant.

In order to use the device 1, a liquid is put into the reservoir 2 and the valve 26 is inserted to close the reservoir 2. The ends of the tube 19 are connected, as needed, to the valve inlet 12 and the reservoir fluid outlet 5. The ends of the tube 20 are connected, as needed, to the valve outlet 13 and the nipple 22 and, specifically, the nipple fluid outlet 21. It will be appreciated that one or more ends of the tube 19 or the tube 20 might be pre-connected to or even integral with the associated structure of the device 1. In the first step of employing the device 1 in a method to transition an infant from non-oral tube feeding to oral nutritive feeding, the nipple 22 is inserted into the infant's mouth while preventing the flow of nutritional fluid from the reservoir 2 through the nipple outlet 21, by closing the valve device 7 to prevent the flow of liquid through the valve body 11. This will acclimate the infant to the nipple 22 and the presence of the nipple 22 in the infant's mouth will encourage the infant to engage in sucking. However, no fluid will enter the infant's mouth. After a suitable acclimation period, for example, 5 to 10 minutes, the valve knob 16 is adjusted, thereby permitting the flow of fluid through the valve 7 to the nipple outlet 21. The valve 7 restricts the flow of fluid so that, no matter how hard the infant sucks, the infant is not able to withdraw fluid at a rate greater than a given rate from the nipple outlet. The given rate is the rate that an infant with poor coordination of the sucking, swallowing and breathing cycle of feeding could handle without distress. For purposes of illustration, the given flow rate might be one that would enable the flow of about 10 cubic centimeters of liquid over a twenty minute period out of the nipple outlet 21, under negative pressure that an infant with good sucking ability could establish. A higher or lower flow rate may be employed at this stage in the method, however. It should be noted that infants salivate and those infants who can swallow their saliva without distress have established at least a minimal degree of coordination of the suck/swallow/breathe pattern required for oral nutritive feeding. The given flow rate can advantageously be a rate that corresponds with the rate of saliva production because this will most likely not be overwhelming to the infant. If it is, the flow can be immediately reduced.

The method comprises additional subsequent feeding regimens wherein, if, during the first feeding regimen, the infant did not receive fluid at a rate which exceeded the infant's ability to swallow that fluid, restriction of the flow of fluid is sequentially gradually relaxed somewhat until the infant is able withdraw at least about sixty cubic centimeters of fluid during a twenty minute feeding without distress. The exact flow rates of sequential feeding regimens is not critical to the method of this invention. What is critical is that when fluid is first introduced through the nipple outlet, it is done at a rate that will not put an infant, even one with poorly coordinated suck/wallow/breathe patters, into distress. It is also critical that the flow rate be slowly and sequentially increased over several feedings at a rate corresponding with, or slower than, the rate at which the infant develops coordination of the suck/swallow/breather pattern needed to move from non-oral tube feeding to oral feeding. It is also critical that if, during the first feeding regimen or subsequent feeding regimens, the infant suffers distress from receiving fluid at a rate which exceeded the infant's ability to swallow, the flow of fluids is promptly restricted to a lower rate until the infant is able to feed without distress at that rate. Thereafter, the flow rate can be sequentially and gradually increased until the infant can take about 60 cubic centimeters of liquid in a twenty minute feeding. Up to that point, non-oral tube feeding will likely be continued. Once that rate is achieved however, non-oral tube feeding can be withdrawn in favor of oral feeding.

Figure 3:
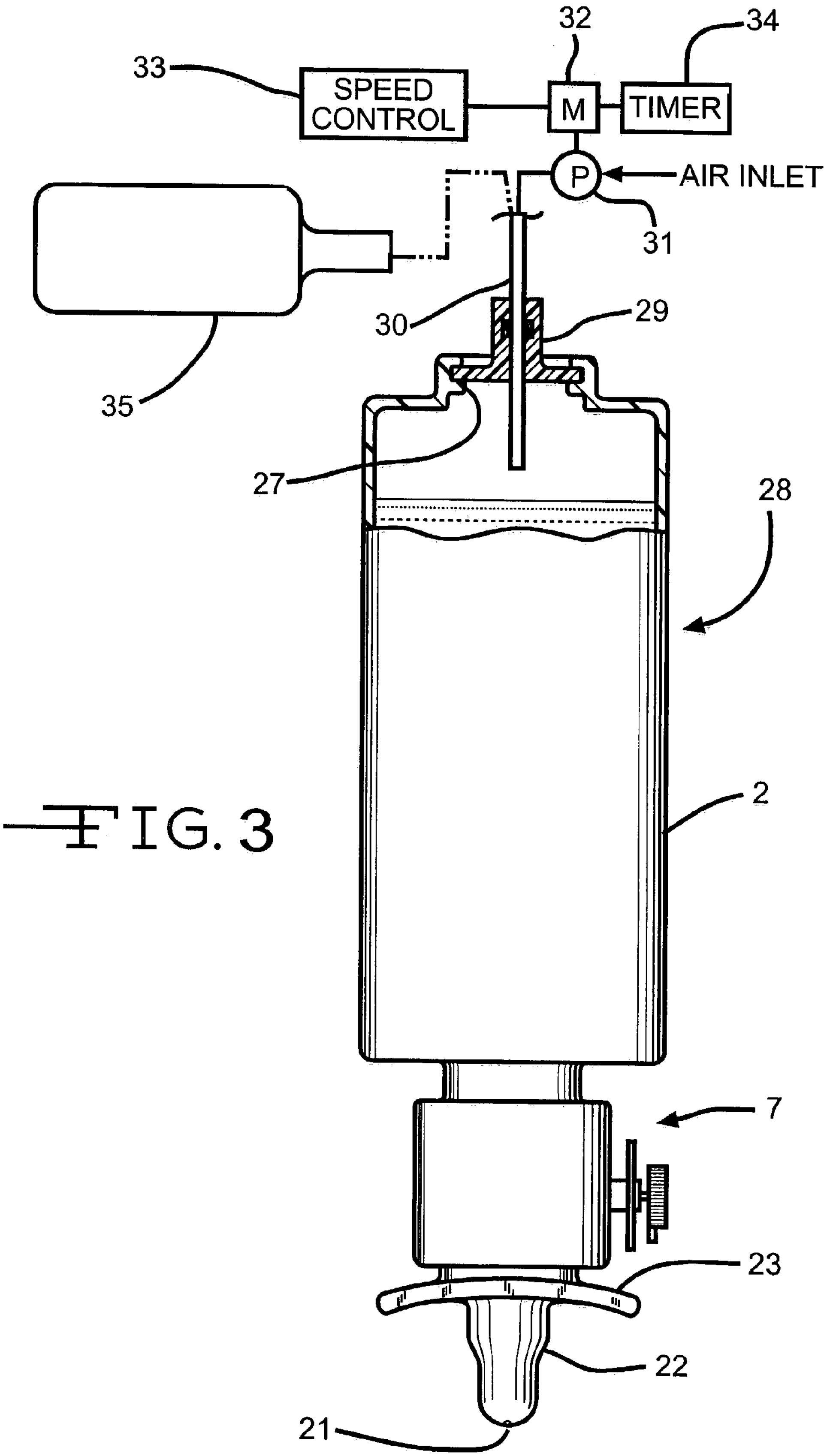
FIG. 3 is a view, partially in cross-section, of the feeding device shown in FIGS. 1 and 2 incorporating additional features.

Referring now to FIG. 3, a feeding device indicated generally at 28 corresponds generally with the feeding device 1 illustrated in FIGS. 1 and 2, except that the air inlet valve 26 has been replaced with a tube support 29 for supporting a tube 30 in the fill passageway 27. One end of the tube 30 extends into the reservoir 2 and the other end of the tube 30 is connected to a pump 31 that can be operated to pump air through the tube 30 to pressurize the inside of the reservoir 2. When the flow of liquid from the reservoir 2 to the nipple fluid outlet 21 is highly restricted, it may be desirable or necessary to deliver fluid from the reservoir 2 to the nipple fluid outlet 21 under a very small amount of pressure, especially in the case where an infant is incapable of creating enough negative pressure around the nipple outlet 21 to withdraw fluid from the nipple 22. It must be remembered, however, that when the flow of liquid to the nipple outlet 21 is highly restricted, it is restricted to prevent the infant from becoming distressed by too much liquid being introduced into the infant's mouth at too fast of a rate. Accordingly, only a very low positive pressure should ever be developed in the reservoir 2, so that the quantity and flow rate of liquid exiting the nipple fluid outlet are low enough to prevent distress for the infant. The pump 31 is powered by a motor 32 and has an air inlet as shown in FIG. 3. A motor speed control 33 and a timer 34 may be operatively associated with the pump 31 to control the quantity and pressure of the air that is pumped through the tube 30 into the reservoir, as desired. As an alternative to the pump 31, a small, hand operated bulb type pump 35 may be connected to the tube so that a care giver can manually pressurize the inside of the reservoir 2.

In sum, the present device promotes and facilitates the transition from non-nutritive sucking on a pacifier, i.e., a nipple with no liquid flow, to nutritive sucking sufficient to sustain the infant. The invention is primarily useful for premature infants that have not learned to take nutrition orally as well as for other medically fragile infants. The feeding device and method are used first to acclimate an infant to a particular nipple and thereafter to administer liquids to the infant, initially, at a very low flow rate so that an infant who is capable of sucking fluid at a substantial flow rate from a nipple but is incapable of coordinating its suck/swallow/breathe pattern to accommodate that flow rate, can take fluid orally without becoming distressed. The present invention permits the oral administration liquids, formula and/or breast milk in a non-threatening and barely detectable manner, initially, with a gradual transition to higher flow rates thereby taking an infant gradually from a functional non-nutritive suck on a pacifier to efficient, nutritive oral feedings from a bottle capable of sustaining the infant. The method of controlling the flow rate and being able to adjust that rate without interrupting the suck, swallow, breathe, burst and pause process is very important. There is a tremendous transition that occurs physiologically between non-nutritive and nutritive sucking. This transition can be extremely overwhelming to the neonate with an immature respiratory system when required to coordinate the suck/swallow/breathe cycle essential for nutritive feeding.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

We claim:

1. A method for wearing an infant from non-oral tube feeding to oral nutritive feeding, said method comprising a first feeding regimen comprising the steps of:

providing a feeding device comprising a resevoir, a nipple with a fluid outlet and an attached shield, a conduit connecting the reservoir to the nipple outlet and a manually adjustable valve for controlling the flow of fluid through the conduit, inserting the nipple into the infant's mouth while essentially preventing the flow of fluid through the nipple outlet during an acclimation period, permitting the flow of fluid through the nipple outlet while restricting the flow of fluid so that no matter how hard the infant sucks, the infant is not able to withdraw fluid at a rate greater than a given rate from the nipple outlet, wherein the given rate is the rate that an infant with poor coordination of the sucking, swallowing and breathing cycle of feeding could handle without distress, said method comprising additional subsequent feeding regimens wherein, if, during the first feeding regimen, the infant did not receive fluid at a rate which exceeded the infant's ability to swallow that fluid, restriction of the flow of fluid is gradually relaxed somewhat until the infant is able to withdraw at least about sixty cubic centimeters of fluid during a twenty minute feeding without destress, wherein if, during the first feeding regimen or subsequent feeding regimens, the infant suffers distress from receiving fluid at a rate which exceeded the infant's ability to swallow, the flow of fluids is restricted to a lower rate until the infant is able to feed without distress and, thereafter, administering said subsequent feeding regimens recited above.

2. A method for introducing an infant to oral nutritive feeding, said method comprising a first feeding regimen comprising the steps of providing a feeding device comprising a reservoir, a nipple with a fluid outlet and an attached shield, a conduit connecting the reservoir to the nipple outlet and a manually adjustable valve for controlling the flow of fluid through the conduit, inserting the nipple into the infant's mouth while essentially preventing the flow of fluid through the nipple outlet during an acclimation period, permitting the flow of fluid through the nipple outlet while restricting the flow of fluid so that no matter how hard the infant sucks, the infant is not able to withdraw fluid at a rate greater than a given rate from the nipple outlet, wherein the given rate is the rate that an infant with poor coordination of the sucking, swallowing and breathing cycle of feeding could handle without distress, said method comprising additional subsequent feeding regimens wherein, if, during the first feeding regimen, the infant did not receive fluid at a rate which exceeded the infant's ability to swallow that fluid, restriction of the flow of fluid is gradually relaxed somewhat until the infant is able to withdraw at least about sixty cubic centimeters of fluid during a twenty minute feeding without distress, wherein if, during the first feeding regimen or subsequent feeding regimens, the infant suffers distress from receiving fluid at a rate which exceeded the infant's ability to swallow, the flow of fluids is restricted to a lower rate until the infant is able to feed without distress and, thereafter, administering said subsequent feeding regimens recited above.

* * * * *